US010485466B2

(12) United States Patent
Faubert et al.

(10) Patent No.: US 10,485,466 B2
(45) Date of Patent: Nov. 26, 2019

(54) DEVICE AND METHOD FOR MEASURING MILD PERCEPTUAL IMPAIRMENT

(75) Inventors: Jocelyn Faubert, Montreal (CA); Armando Bertone, Montreal (CA)

(73) Assignee: COGNISENS INC., Montreal, Québec (CA)

(*) Notice: Subject to any disclaimer, the term of this patent is extended or adjusted under 35 U.S.C. 154(b) by 1402 days.

(21) Appl. No.: 13/257,670

(22) PCT Filed: Mar. 19, 2010

(86) PCT No.: PCT/CA2010/000439
§ 371 (c)(1),
(2), (4) Date: Nov. 23, 2011

(87) PCT Pub. No.: WO2010/105370
PCT Pub. Date: Sep. 23, 2010

(65) Prior Publication Data
US 2012/0059229 A1    Mar. 8, 2012

Related U.S. Application Data

(60) Provisional application No. 61/202,632, filed on Mar. 20, 2009.

(51) Int. Cl.
*A61B 5/16* (2006.01)
*A61B 5/00* (2006.01)
(52) U.S. Cl.
CPC ............ *A61B 5/161* (2013.01); *A61B 5/4076* (2013.01); *A61B 5/4088* (2013.01)

(58) Field of Classification Search
CPC .................... A61B 5/16–18; A61B 5/4088
See application file for complete search history.

(56) References Cited

U.S. PATENT DOCUMENTS

| 5,617,872 | A  | 4/1997  | Scinto et al.    |
|-----------|----|---------|------------------|
| 6,109,107 | A  | 8/2000  | Wright et al.    |
| 6,315,412 | B1 | 11/2001 | Snodderly et al. |
| 6,485,417 | B1 | 11/2002 | Bowles et al.    |
| 6,702,757 | B2 | 3/2004  | Fikushima et al. |

(Continued)

FOREIGN PATENT DOCUMENTS

| CN | 1934596 A    | 3/2007 |
|----|--------------|--------|
| EP | 2036486 A1   | 3/2009 |

(Continued)

OTHER PUBLICATIONS

Notice of Reasons for Rejection issued from the Japanese Patent Office in corresponding application 2012-500022, dated Jun. 2, 2014.

(Continued)

*Primary Examiner* — Adam J Eiseman
(74) *Attorney, Agent, or Firm* — Praxis

(57) ABSTRACT

A device and method for measuring mild perceptual impairment of a human subject, in which a stimulus having at least one parameter is applied to the human subject. The human subject produces a response to the stimulus indicative of a perception by the human subject of the at least one parameter of the stimulus. The response of the human subject is then processed in view of determining if the human subject suffers from mild perceptual impairment.

13 Claims, 6 Drawing Sheets

(56) References Cited

U.S. PATENT DOCUMENTS

| | | | |
|---|---|---|---|
| 7,211,050 B1* | 5/2007 | Caplygin | A61B 5/168 |
| | | | 351/222 |
| 7,972,278 B2* | 7/2011 | Graham | A61B 5/04842 |
| | | | 600/544 |
| 2002/0099305 A1* | 7/2002 | Fukushima | A61B 3/112 |
| | | | 600/558 |
| 2002/0143240 A1 | 10/2002 | Teicher et al. | |
| 2004/0167380 A1 | 8/2004 | Simon | |
| 2005/0101877 A1 | 5/2005 | Miller et al. | |
| 2006/0189885 A1 | 8/2006 | Yelland et al. | |
| 2011/0063571 A1* | 3/2011 | Duffy | A61B 3/022 |
| | | | 351/239 |

FOREIGN PATENT DOCUMENTS

| | | |
|---|---|---|
| JP | 08-168466 A | 7/1996 |
| JP | 8168466 | 7/1996 |
| JP | H10-503209 A | 3/1998 |
| JP | H11-332855 A | 12/1999 |
| JP | 2004-527295 A | 9/2004 |
| JP | 2005-185395 A | 7/2005 |
| JP | 2006-014902 A | 1/2006 |
| RU | 2006115408 A | 11/2007 |
| WO | 03051199 A1 | 6/2003 |
| WO | 2007112474 A1 | 10/2007 |

OTHER PUBLICATIONS

Muckli L. et al.: "Cerebral correlates of impaired grating perception in individual, psychophysically assessed human amblyopes", Vision Research, Pergamon Press, Oxford, GB, vol. 46, No. 4, Feb. 1, 2006, pp. 506-526, XP025009876.

Supplementary European Search Report issued from the European Patent Office in corresponding application No. 10753054.5, dated Oct. 17, 2014.

Cronin-Golomb A. et al. "Visual dysfunction in Alzheimer's disease: Relation to normal aging" Annals of Neurology vol. 29, No. 1, pp. 41-52, Jan. 1991.

Zaccara G. et al. "Smooth-pursuit eye movements: alterations in Alzeimer's disease" Journal of Neurological Sciences vol. 112/1-2, pp. 81-89, 2003.

Allard, R., et al. (2006). "Same calculation efficiency but different internal noise for luminance- and contrast- modulated stimuli detection." Journal of Vision, 6(4), 322-334, http://iournalofvision.Org/6/4/3/. doklO.1 167/6.4.3.

Bertone A et al. (2006) "The impact of blurred vision on cognitive assessment" Journal of Clinical and Experimental Neuropsychology.

Bertone A et al. (2006). "Demonstrations of decreased sensitivity to complex motion information not enough to propose autism-specific neural etiology." Journal of Autism and Developmental Disorders, 36, 55-64.

Bertone A et al. (2003). "Motion perception in Autism: A 'complex' issue." Journal of Cognitive Neuroscience, 15, 218-225.

Bertone A, et al.(2005). "Enhanced and diminished visuo-spatial information processing in autism depends on stimulus complexity." Brain, 128, 2430-2441.

Brosseau-Lachaine, O. et al. (2008) "Mild traumatic brain injury induces prolonged visual processing deficits in children." Brain Injury, 22(9), 657-668.

Faubert, J. (2002) "Visual perception and aging." Canadian Journal of Experimental Psychology, 56, 164-176.

Habak, C. et al. (2000). "Larger effect of aging on the perception of higher-order stimuli" Vision Research, 40(8), 943-950.

Karwatsky P et al.(2006). "Defining the Nature of Motion Perception Deficits in Glaucoma Using Simple and Complex Motion Stimuli." Optometry and Vision Science, 83, 466-472.

Kogan CS et al. (2004). "Integrative cortical dysfunction and pervasive motion perception deficit in fragile X syndrome." Neurology, 63, 1634-1639.

Thibault, D. et al. (2007) "Maturation of the sensitivity for luminance and contrast modulated patterns during development of normal and pathological human children." Vision Research, 47(12)1561-9.

H. Levitt, "Transformed Up-Down Methods in Psychoacoustics", The Journal of the Acoustical Society of America, vol. 49, No. 2 (Part 2), 1971, pp. 467-477.

* cited by examiner

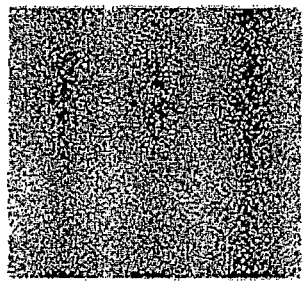
FIG: 2a
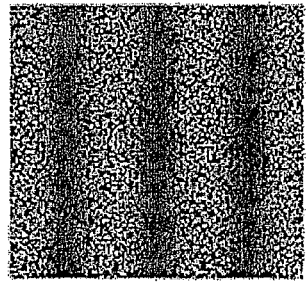
FIG: 2c
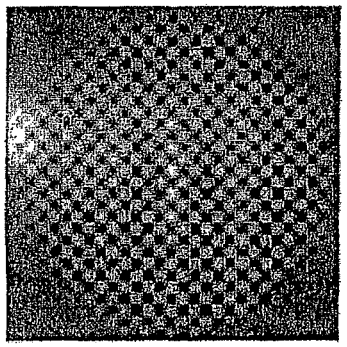
FIG: 2b
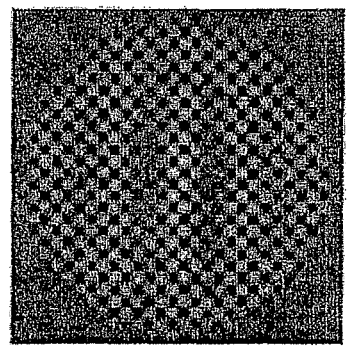
FIG: 2d

DEVICE AND METHOD FOR MEASURING MILD PERCEPTUAL IMPAIRMENT

FIELD

The present invention relates to a device and a method for measuring mild perceptual impairment (MPI) of a human subject that can be used, for example, as a screening, monitoring and/or diagnostic measure for various neurobiological alterations including brain trauma, Alzheimer's disease and Autism.

BACKGROUND

Research has been conducted for a number of years to detect early perceptual changes caused by subtle neurobiological alterations (NBAs) such as normal aging, neurotoxicity, glaucoma and more recently autism, fragile x, mild brain injuries and stroke.

The rationale for these studies was to fill a void of scientific knowledge related to perceptual functions, which resides between basic sensory measures, such as visual acuities, and higher cognitive measures such as neuropsychological profiles. Basic sensory measures are used to establish the attenuation of peripheral sensory mechanisms of the eye and ears while higher cognitive measures attempt to characterize cortical anomalies or symptoms. In fact, perceptual processing precedes cognitive processing and is often considered to be low-level cognitive processing although it is never systematically and explicitly assessed in neurological or neuropsychological evaluations.

Over the years, substantial evidence has been accumulated that, under appropriate conditions, perceptual changes are very good measures of neurobiological alterations and are resistant to lower-level and higher-level confounds in aging (Faubert, (2002)). In recent years, it has also been demonstrated that perceptual assessment techniques are also very sensitive to other NBAs such as autism (Bertone, Mottron, Jelinic, Faubert ((2003) and (2005))), fragile x (Kogan, Bertone, Cornish, Boutet, Der Kaloustian, Andermann, Faubert, Chaudhuri (2004)) and mild traumatic brain injuries (Brosseau-Lachaine, Gagnon, Forget & Faubert (2008)).

To introduce such measures in the clinical environment, it was proposed to develop visual charts for assessing both simple and complex perceptual processing. The problem with such charts is one of calibration of the image to obtain appropriate and constant linearization, levels of contrast, and the fact that it is not possible to establish perceptual signatures as described below because both static and dynamic stimuli are needed.

Accordingly, there exists a need for a device and method to implement measures of neurobiological alterations in the clinical environment and for various applications.

SUMMARY

According to a first aspect of the invention, there is provided a method of measuring mild perceptual impairment of a human subject, comprising: applying to the human subject a stimulus having at least one parameter; production, by the human subject, of a response to the stimulus indicative of a perception by the human subject of the at least one parameter of the stimulus; and processing the response of the human subject in view of determining if the human subject suffers from mild perceptual impairment.

According to a second aspect of the invention, there is provided a device for measuring mild perceptual impairment of a human subject, comprising: means for generating a stimulus for application to the human subject, the stimulus having at least one parameter; means operated by the human subject for producing a response to the stimulus indicative of a perception of the at least one parameter of the stimulus by the human subject; and a processor of the response of the human subject in view of determining if the human subject suffers from mild perceptual impairment.

According to a third aspect of the invention, there is provided a device for measuring mild perceptual impairment of a human subject, comprising: a generator of stimulus for application to the human subject, the stimulus having at least one parameter; a producer, for operation by the human subject, of a response to the stimulus indicative of a perception of the at least one parameter of the stimulus by the human subject; and a processor of the response of the human subject in view of determining if the human subject suffers from mild perceptual impairment.

The foregoing and other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

In the appended drawings:

FIG. 2a is a first example of first-order stimulus that can be used for detecting/monitoring/screening of neurobiological disorders such as Alzheimer;

FIG. 2b is a second example of first-order stimulus that can be used for detecting/monitoring/screening of neurobiological disorders such as Alzheimer;

FIG. 2c is a first example of second-order stimulus that can be used for detecting/monitoring neurobiological disorders such as Alzheimer;

FIG. 2d is a second example of second-order stimulus that can be used for detecting/monitoring neurobiological disorders such as Alzheimer;

DETAILED DESCRIPTION

Figure 1:
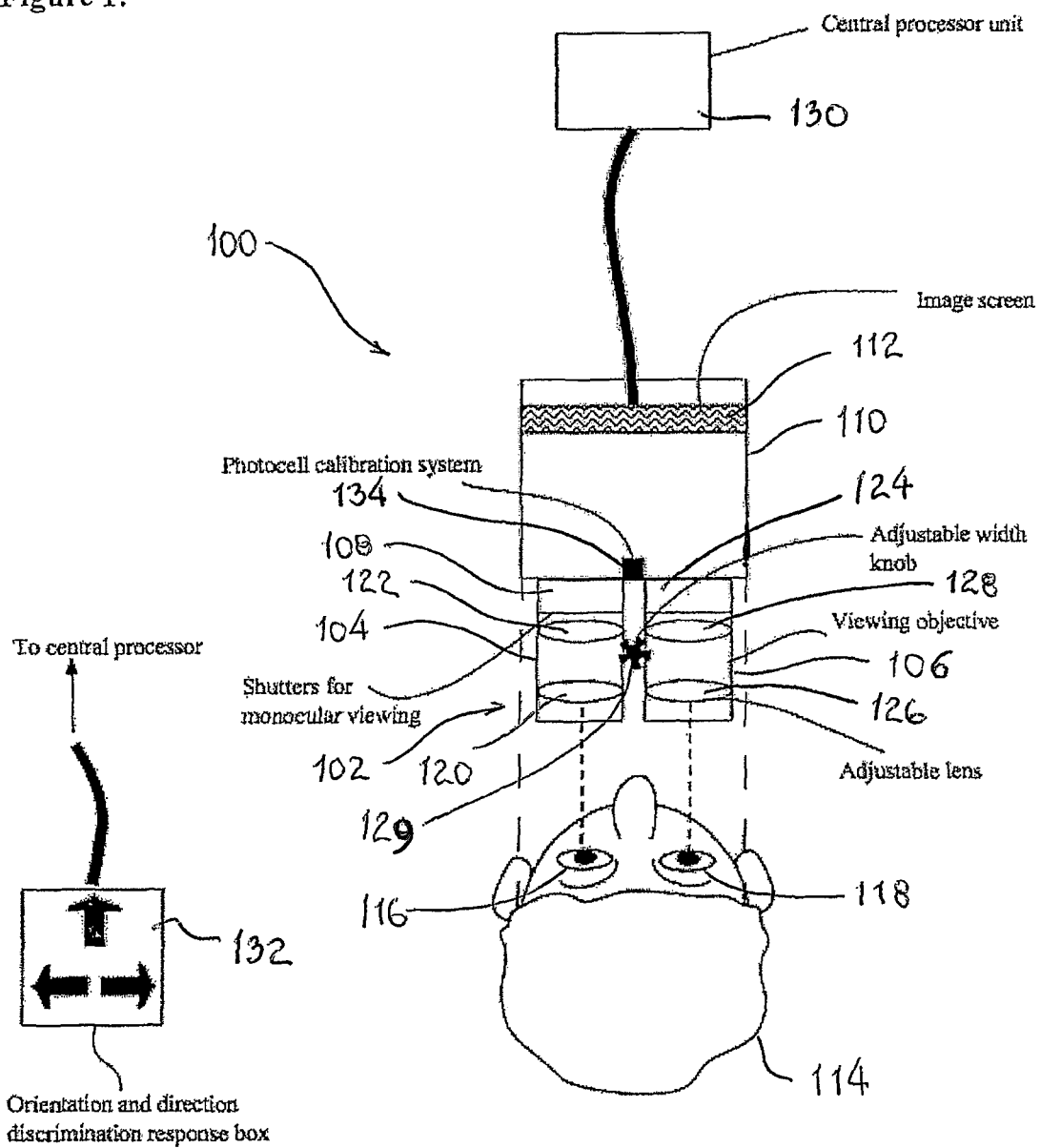
FIG. 1 is a schematic plan view of an example of device for measuring mild perceptual impairment (MPI)

Referring to FIG. 1, a device 100 for measuring mild perceptual impairment (MPI) is schematically illustrated.

The device 100 for measuring mild perceptual impairment comprises a generator of stimulus for application to a human subject, the stimulus having at least one parameter. The generator of stimulus comprises a box-like enclosure 110 and a screen 112 mounted in the box-like enclosure 110 for displaying an image, more specifically an image stimulus. For example, the screen 112 may comprise a LCD (Liquid Crystal Display) screen, a plasma screen, AMLCD, LCOS, OLED, MEMS, etc. Although the generator of stimulus of the device 100 may comprise a single screen 112 as illustrated in FIG. 1, this single screen 112 could also be replaced by two separate screens (not shown), including a first screen seen by the left eye 116 of the human subject 114 and a second screen seen by the right eye 118 of the human subject 114.

The generator of stimulus of the device 100 for measuring mild perceptual impairment further comprises binoculars 102 including a left viewing objective 104 and a right viewing objective 106. As shown in FIG. 1, the binoculars 102 allow the human subject 114 to look at the image stimulus displayed on the screen 112. More specifically, the left eye 116 of the human subject 114 looks at the image stimulus through the left viewing objective 104 while the right eye 118 of the human subject 114 looks at the image stimulus through the right viewing objective 106.

The binoculars 102 further comprise an adjustable width knob 129. The adjustable width knob 129 is associated with a mechanism for adjusting the lateral spacing between the left 104 and right 106 viewing objectives to the spacing between the left 116 and right 118 eyes of the human subject 114. Such a mechanism is well known to those of ordinary skill in the art and, therefore, will not be further described in the present specification.

The left viewing objective 104 comprises proximal and distal ends. A shutter 108 is mounted in the left viewing objective 104 at the proximal end thereof. The shutter 108 can be operated between a closed position and an open position. In the open position of the shutter 108, the left eye 116 of the human subject 114 is allowed to see the image stimulus on the screen 112 while in the closed position of the shutter 108, the left eye 116 of the human subject 114 is prevented from seeing the image stimulus on the screen 112.

A longitudinally adjustable lens 120 is also mounted in the left viewing objective 104 at the distal end thereof. Finally, a stationary lens 122 is mounted in the left viewing objective 104 next to the shutter 108 between the shutter 108 and the longitudinally adjustable lens 120.

In the same manner, the right viewing objective 106 comprises proximal and distal ends. A shutter 124 is mounted in the right viewing objective 106 at the proximal end thereof. The shutter 124 can be operated between a closed position and an open position. In the open position of the shutter 124, the right eye 118 of the human subject 114 is allowed to see the image stimulus on the screen 112 while in the closed position of the shutter 124, the right eye 116 of the human subject 114 is prevented from seeing the image stimulus on the screen 112.

A longitudinally adjustable lens 126 is mounted in the right viewing objective 106 at the distal end thereof. Finally, a stationary lens 128 is mounted in the right viewing objective 106 next to the shutter 124 between the shutter 124 and the longitudinally adjustable lens 126.

Operation of the shutters 108 and 124 of the left 104 and right 106 viewing objectives between their open and closed positions will enable conduction of tests on the human subject 114 in which the left eye 116 only (monocular viewing), the right eye 118 only (monocular viewing) or both the left eye 116 and the right eye 118 of the human subject 114 are allowed to see the image stimulus displayed on the screen 112.

The device 100 for measuring mild perceptual impairment (MPI) further comprises a central processing unit, hereinafter processor 130 connected to the screen 112 for controlling display of image stimuli on that screen 112. More specifically, the processor 30 forms part of the generator of stimulus to generate and display different image stimuli (images) on the screen 112. Examples of image stimuli are illustrated in FIGS. 2a-2d; these image stimuli can be used for detecting/monitoring/screening neurobiological disorders such as Alzheimer.

FIG. 2a is a first example of a first-order image stimulus, more specifically vertical bars formed by luminance contrast and that can be used for detecting/monitoring neurobiological disorders such as Alzheimer. FIG. 2b is a second example of first-order image stimulus, more specifically vertical bars formed by luminance contrast in an octagonal shape built of light and dark squares, and that can be used for detecting/monitoring neurobiological disorders such as Alzheimer. FIG. 2c is a first example of second-order image stimulus, more specifically vertical bars formed by texture contrast and that can be used for detecting/monitoring neurobiological disorders such as Alzheimer. FIG. 2d is a second example of second-order image stimulus, more specifically vertical bars formed by texture contrast in an octagonal shape built of light and dark squares, and that can be used for detecting/monitoring neurobiological disorders such as Alzheimer.

For measuring mild perceptual impairment (MPI), the human subject 114 is required to look at the image stimulus displayed on the screen 112 of the MPI measuring device 100 by placing his left 116 and right 118 eyes in front of the left 104 and right 106 viewing objectives of the binoculars 102. The lateral spacing between the left 104 and right 106 viewing objectives can be adjusted to the spacing between the left 116 and right 118 eyes of the human subject 114 through the above described adjustable width knob 129 and corresponding mechanism (not shown). The positions of the longitudinally adjustable lenses 120 and 126 can then adjusted individually through appropriate mechanisms (not shown) for best viewing (focus) of the image stimulus displayed on the screen 112 by the respective left 116 and right 118 eyes of the human subject 114. Such mechanisms for longitudinally adjusting the positions of the lenses 120 and 126 are well known to those of ordinary skill in the art and, therefore, will not be further described in the present specification.

The human subject 114 then looks at the image stimulus displayed on the screen 112 and is required to make decisions about what he/she sees. The decisions require simple judgment. For example, the human subject 114 will respond by indicating whether the bars of FIG. 2a, 2b, 2c or 2d are vertical or horizontal. Therefore, according to a non-limitative alternative, the bars of FIGS. 2a-2d of the image displayed on the screen 112 could be horizontal. Vertical bars can be moved to the left or to the right, or horizontal bars can be moved upwardly or downwardly. Another possible decision or response from the human subject 114 is to indicate the direction of movement of the bars, i.e. toward the left or the right, respectively upwardly or downwardly. A rotational movement of the bars can also be induced and the decision or response of the human subject would then be whether the bars are rotating clockwise or counterclockwise. Another possible response could be a choice made by the human subject 114 between different shapes displayed on the screen 112. The human subject 114 can also be required to determine whether a given target appears in a first or second image presented on the screen 112, each image being preceded by a sound cue.

A producer of a response of the human subject 114 to the image stimulus comprises an orientation and direction discrimination response box 132 (FIG. 1) itself comprising a suitable keyboard to allow the human subject 114 to enter his/her responses, for example at least one of the following responses: whether the bars of FIG. 2a, 2b, 2c or 2d displayed on the screen 112 are vertical or horizontal, whether the vertical bars displayed on the screen 112 move toward the left or the right or the horizontal bars displayed on the screen 112 move upwardly or downwardly, whether the bars displayed on the screen 112 are rotating clockwise or counterclockwise, regarding shapes displayed on the screen 112 whether a given target appears in a first or second image presented on the screen 112, etc. The orientation and direction discrimination response box 132 is connected to the processor 130 to supply the responses of the human subject 114 to the image stimulus to that processor 130. The responses of the human subject 114 entered through the orientation and direction discrimination response box 132 are recorded in the processor 130 for example for further analysis thereof.

First- and second-order properties of the image stimuli displayed on the screen 112 are defined by at least one parameter such as luminance and texture contrast. The processor 130 can manipulate the at least one parameter and, then, can determine perceptual sensitivity of the human subject 114 in relation to the at least one manipulated parameter. Based on the responses of the human subject 114 for the at least one parameter of the image stimuli or different combinations of parameters of the image stimuli, it is possible to establish whether the patient suffers from mild perceptual impairment (MPI) which can precede mild cognitive impairment (MCI). Given an MPI detection, it is further possible to establish the perceptual signature (PS) of the human subject 114 that can be used to help neurologists and/or other clinicians to establish the type of neurobiological alteration the human subject 114 may have. Similar device and method can use first-order and second-order stimuli implemented in the auditory and tactile domains.

In a typical testing condition, the human subject 114 is asked to respond, through the orientation and direction discrimination response box 132, whether a series of bars that are displayed on the screen 112 are vertical or horizontal in a static condition and whether the bars are moving toward the left or the right in a dynamic condition while the processor 130 systematically manipulates the luminance or texture contrast with an adaptive staircase procedure generating threshold measures. Typical session takes about five (5) to ten (10) minutes of testing.

For example, the generator of stimulus may further comprise a photocell calibration system 134 mounted in the box-like enclosure 110 of FIG. 1 in front of the display surface of the screen 112. Feedback is provided from the photocell calibration system to the processor 130 for calibrating the MPI measuring device 100 as a function of the at least one parameter of the image stimulus displayed on the screen 112 such as luminance and texture contrast.

More specifically, the photocell calibration system 134 as illustrated in FIG. 1 may comprise luminance sensors that sweep the display surface of the screen 112. The processor 130 may then be responsive to the readings from the luminance sensors to generate auto-calibration procedures for the screen 112 that introduce required corrections to linearize the output (luminance of the image stimulus) of the screen 112.

As indicated in the foregoing description, by establishing early perceptual changes caused by subtle neurobiological alterations (NBAs) such as normal aging, neurotoxicity, glaucoma and more recently autism, fragile x, mild brain injuries and stroke, it is possible to fill a void of scientific knowledge related to perceptual functions, which reside between basic sensory measures, such as visual acuities, and higher cognitive measures such as neuropsychological profiles. Basic sensory measures are used to establish the attenuation of peripheral sensory mechanisms of the eye and ears while the higher cognitive measures attempt to characterize cortical anomalies or symptoms. In fact perceptual processing precedes cognitive processing and is often considered as low-level cognitive processing although it is never systematically assessed in neurological or neuropsychology evaluations. Under appropriate conditions, perceptual changes are very good measures (or they correlate well to) of neurobiological alterations and are resistant to lower- and higher-level confounds in aging. It has also been demonstrated that perceptual assessments techniques are also very sensitive to other NBAs such as autism, fragile x and mild traumatic brain injuries. The device and method according to the invention is not only sensitive, but also specific to different NBAs and help to distinguish between neural etiologies by using perceptual signatures (Bertone & Faubert, 2006).

A "perceptual signature" is a characteristic pattern of performance determined by measuring the sensitivity of the human subject to static and dynamic stimuli (i.e., gratings) that are defined by either simple (luminance) or complex (texture) attributes. The latter type of stimuli necessitates neuro-integrative processing to be perceived whereas the former type is processed by standard neural analysis. In the visual domain, subtle NBAs would affect the sensitivity to complex, texture-defined stimuli but not to simple, luminance-defined stimuli. Such a signature is what defines MPI. In addition, perceptual signatures are consistent with distinct neural etiologies defined by different types of NBAs, even for conditions sharing behavioral phenotypes such as autism and fragile-x syndrome (Bertone & Faubert, 2006).

Perceptual signatures can be used concurrently with more traditional methods of cognitive assessment (i.e., neuropsychological testing) currently used to build cognitive profiles used for diagnosis of variously neurological conditions. Although regarded as predominantly a screening tool for NBAs, the device and method according to the invention has certain advantages over traditional paper-pencil neuropsychological tasks. First, given the simplicity of its measure (i.e., judging the orientation of a bar), results are much less biased as a function of level of education as most conventional tasks. Second, neuropsychological testing is limited by the ocular status of the person being assessed. Specifically, performance on non-verbal (or visual) tasks significantly decreases when visual acuity is even minimally affected (i.e., 20/40) (Bertone, Bettinelli, Faubert, 2006). This is especially evident for persons over the age of 65, the target age range for persons with dementia. The proposed device circumvents this important problem by incorporating a built-in optical system that corrects for accommodation and individual refraction.

The device and method according to the present invention may incorporate different signal patterns (called carriers as shown in FIGS. 2a-2d) that generate different levels of internal neural noise levels as evidenced by ideal observer modeling and psychophysical results (Allard & Faubert, 2006). This allows to use a specific pattern that is optimized for very early detection of MPIs (Gaussian noise; Habak & Faubert, 2000), and other patterns for monitoring the processes at early stages (binary noise) and later stages (plaid texture).

Other possible functions of the processor 130 are the following:

The processor 130 may calculate contrast thresholds and sensitivity measures related to the responses of the human subject 114 entered on the box 132 in response to the various image or other stimuli;

The processor 130 may perform statistical analysis by comparing the responses of the human subject 114 entered on the box 132 in response to the various image or other stimuli, to representative population means to establish normality of abnormality values;

The processor 130 may calculate, produce and supply charts, graphs, tables, etc. showing the information data regarding the responses of the human subject 114 entered on the box 132 in response to the various image or other stimuli, for example evaluation by a physician, neurologist or other medical professional; and The processor 130 may transmit the information data regarding the responses of the human subject 114 entered on the box 132 in response to the various image or other stimuli, to a central server when required or necessary.

Although the above described non restrictive, illustrative embodiment uses a visual device and method, auditory and tactile devices and methods using the same signal and testing strategies can be created.

Possible applications of the device and method for measuring mild perceptual impairment, amongst others, comprise the following:

Determination of neurobiological ability related to driving and piloting skills.

Determination of neurobiological ability related to sports skills particularly after a concussion.

Distinguishing between autism and fragile x in early development (although this is implicit in the "perceptual signature concept".

Determination of neurobiological ability related to learning skills and disability in children.

Etc.

Additional Example of Image Stimuli

The following description relates to other examples of image stimuli that can be used in the above described method and device for measuring mild perceptual impairment of a human subject.

Healthy aging induces several physiological, perceptual and cognitive changes. At the level of the visual system, several visual functions decrease with advancing age, such as contrast sensitivity, visual acuity and perceptual processing. A general agreement is that optical factors are not responsible for all visual function reduction and that neural processing alterations may occur.

As described hereinabove, motion perception can be induced through first- and second-order variations of the spatiotemporal properties of an image. First-order image stimuli are defined by local variations of a parameter, the luminance. In contrast, second-order image stimuli are those defined by parameters other than luminance, for example contrast, polarity and orientation, requiring global integration as well as analysis of the spatial structure of the image to be perceived. Higher level cortical processing required for second-order motion perception suggests a certain level of cortical dissociation between first- and second-order processing.

In a first experiment, contrast sensitivities to motion direction of first-order and fractal rotation were measured for older and younger adult age groups. Fractal rotation was chosen as second-order motion image stimulus to generate image stimuli composed exclusively of low spatial frequencies. The use of a low-pass spatial filter within the image stimuli ensures that the observed reduction in contrast sensitivity to motion direction is attributable to the effect of age on motion integration, rather than to diminished visibility of the presented image stimuli.

Figure 3A:
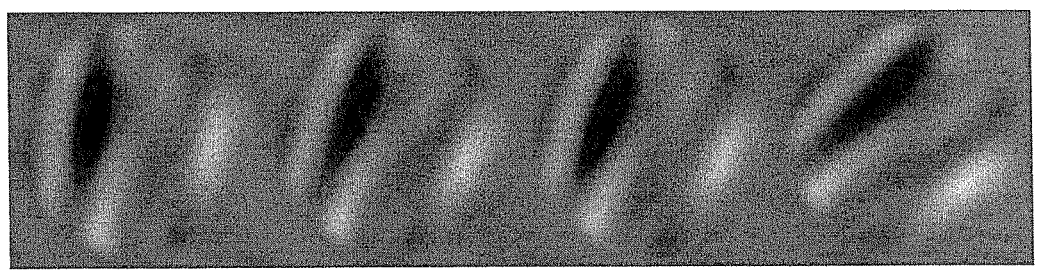
FIG. 3a is an example of a first-order rotation image stimulus showing a sequence of four (4) frames, wherein the image stimulus is rotating clockwise and wherein a single noise frame is rotated in time.
Figure 3B:
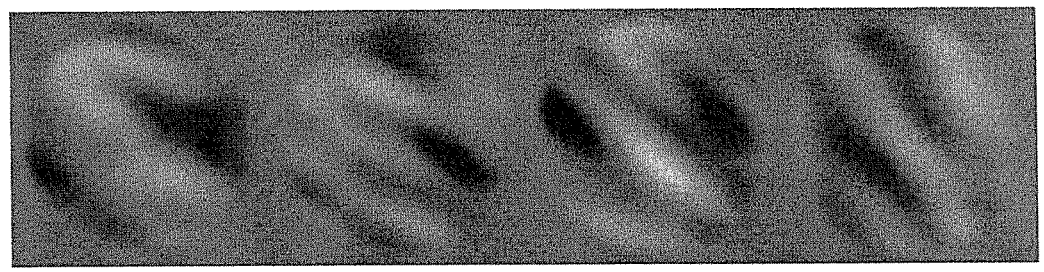
FIG. 3b is an example of fractal rotation image stimulus, showing a sequence of four (4) frames, wherein the stimulus is rotating clockwise and wherein noise is resampled on every presented frame.

More specifically, in the first experiment, two types of stimuli were presented, for example displayed on the screen 112 (FIG. 1): first-order (FIG. 3a) and fractal (FIG. 3b) rotation. Fractal rotation was analyzed by higher-order sensitive mechanisms.

The fractal rotation image stimuli were built using a noise pattern with low pass amplitude spectra corresponding to what is observed in natural images. Noise was resampled in each frame. An orientation filter was applied to each presented noise frame, to make the image spatial structure rich in orientation cues. To perceive rotation, the human subject needs to integrate changes in the spatial structure over time, rather than local luminosity variations. Low spatial filtering of the presented stimuli ensured that differences in motion direction sensitivities were attributable to motion perception, rather than selective age-related contrast sensitivity losses for high spatial frequency patterns. Also, the testing conditions ensured equal stimulus visibility for the younger and older adult age groups.

The same stimulus parameters as for fractal rotation were used for first-order rotation, except that a single noise frame was generated.

In the first experiment, the task of the human subjects consisted in identifying a direction of rotation, i.e. clockwise or counterclockwise using, for example, the orientation and direction discrimination response box 132 (FIG. 1). The image stimuli were viewed binocularly by the subjects.

Figure 4:
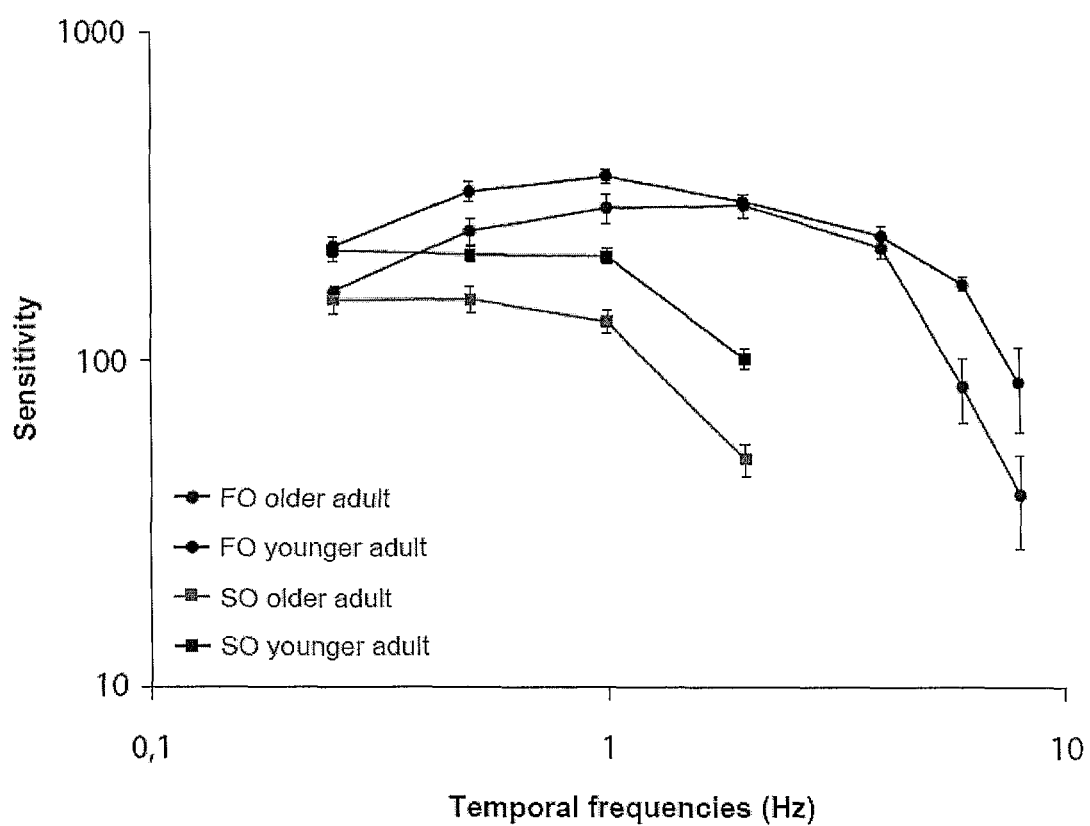
FIG. 4 is a graph showing mean contrast sensitivity to direction discrimination of first-order (FO) and fractal (SO) rotation stimuli as a function of temporal frequency, in which results for older and younger adult age groups are presented.

Contrast thresholds for discrimination of direction of first-order and fractal rotation stimuli were obtained for each participant (human subject) as a function of temporal frequencies. Results for both younger and older adult age groups are presented in the graph of FIG. 4. The results of FIG. 4 are expressed in terms of contrast sensitivity, which was defined as the reciprocal of the contrast threshold. The temporal frequency sensitivity function of first-order rotation was band-pass, whereas that of fractal rotation was low-pass in nature. The results of FIG. 4 suggest that first-order rotation and fractal rotation stimuli are analyzed by first- and second-order sensitive mechanisms, respectively. As can be seen, lower contrast sensitivities for low (i.e. 0.25, 0.5, 1 Hz) and high temporal frequencies (6, 8 Hz) for the first-order stimuli can be observed for the older adult age group. Here the term Hz refers to the number of circle rotations (360 degrees) per second not the number of cycles per second for the sinewave stimuli presented above. Similarly, lower contrast sensitivities at all temporal frequencies, for second-order motion stimuli, were recorded for the older adult age group as compared to the younger adult age group. Findings indicate significant effect of age on perception of direction of first-order rotation at low and high temporal frequencies, as well as to fractal rotation at all temporal frequencies, as evidenced by lower contrast sensitivity values at those testing conditions.

More specifically, the first experiment demonstrates age-related decrease sensitivity to direction of all fractal rotation conditions and some first-order motion conditions. However, the observed increase in contrast thresholds to these motion stimuli could potentially be induced by a reduction in contrast sensitivity to the filtered noise frames used for first-order and fractal rotation stimuli. To differentiate between the potential age-related decreases in contrast sensitivity to noise frame and to direction of first- and second-order motion, an orientation discrimination task of static replicas of first-order and fractal stimuli used in the first experiment has been conducted. Age-related deficits in orientation discrimination for small differences in image stimuli orientation, for example 12°, has been observed in condition of low, but not high, external noise. Moreover, no age-related deficit of contrast sensitivity to orientation would be observed for large differences in grating orientation, i.e. 90°. The following, second experiment verifies whether these findings replicate to orientation discrimination of first-order and fractal rotation static replicas.

Figure 5A:
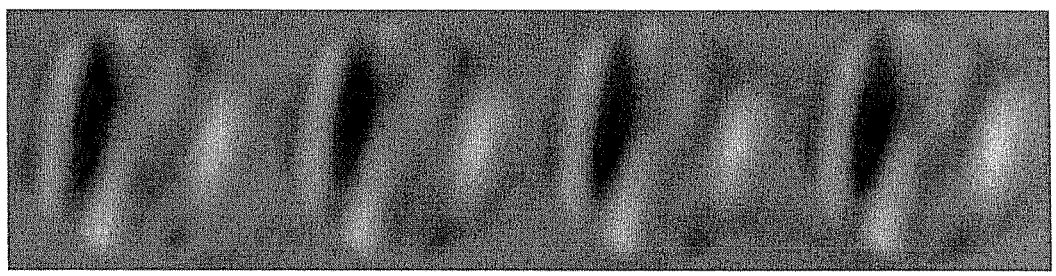
FIG. 5a is an example of image stimulus presented in first-order control condition, showing a sequence of four (4) frames on a single interval, wherein a single noise frame is generated and the presented image stimulus is vertical.
Figure 5B:
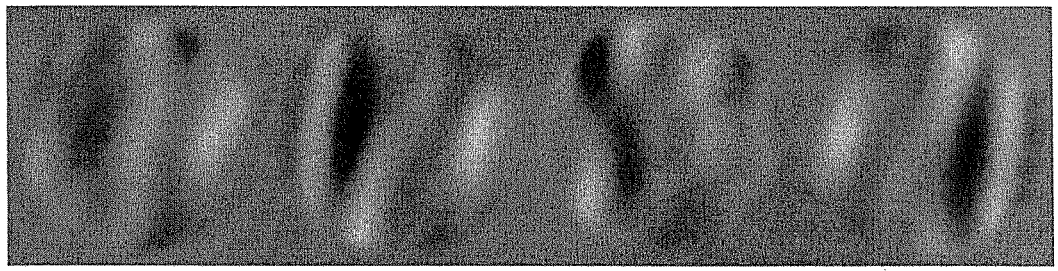
FIG. 5b is an example of image stimulus presented in fractal control condition, showing a sequence of four (4) frames on a single interval, wherein noise is resampled on every presented frame, a flickering pattern is obtained, and the presented image stimulus is vertical.

Replicas of first-order (FIG. 5a) and fractal (FIG. 5b) rotation stimuli used in the first experiment were presented to human subjects, for example on the screen 112 (FIG. 1), except that in the second experiment temporal frequency was 0. Also, a single noise frame was generated as first-order rotation control condition. For fractal rotation control image stimulus, noise was refreshed for every presented noise frame, as defined in the first experiment, resulting in a flickering pattern. For both stimuli, orientation of the spatial filter was randomly assigned a value of 0 or 90°±20°. Both stimuli used in this control condition were accessible to first-order sensitive mechanisms.

Figure 6:
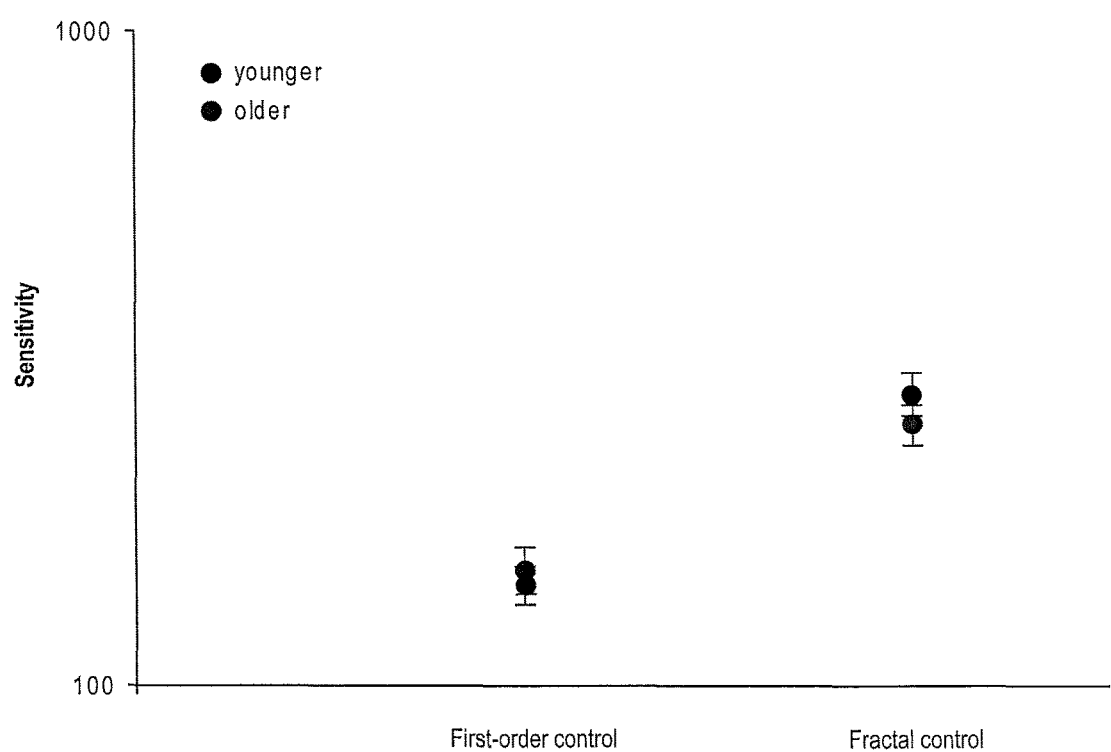
FIG. 6 is a graph showing mean contrast sensitivity to orientation discrimination on both first-order and fractal control conditions, showing results for both older and younger adult age groups.

In the second experiment, the task of the human subjects consisted in identifying whether the presented noise pattern was horizontal or vertical using, for example, the orientation and direction discrimination response box 132 (FIG. 1). For each observer, contrast sensitivity for first-order and fractal rotation controls was obtained. The results are presented in the graph of FIG. 6. Independent samples t-test, performed on logarithmic transformed contrast values, indicate no significant effect of age on contrast thresholds for discrimination of orientation of both first-order and fractal rotation controls. Moreover, as can be seen in the graph of FIG. 6, sensitivity to orientation discrimination was greater for fractal than first-order controls.

Results obtained in the first experiment indicate that aging induces decreased sensitivity to direction identification of both first- and higher-order complex motion. Reduced sensitivity was observed even using stimuli rich in low spatial frequencies. However, impairment in discrimination of direction was affected for all fractal rotation conditions but for only some first-order motion conditions. As demonstrated in the second experiment, age-related decrease of first- and second-order motion perception is not attributable to decreased visibility of the stimuli being used.

Aging induces a systematic reduction in sensitivity to higher-order motion perception at all temporal frequencies, as opposed to first-order perception. It can be concluded that age-related loss in direction sensitivity is more pronounced for second- than for first-order motion stimuli. Findings from the first and second experiments point to an age-related decrease of sensitivity to second-order motion perception, the visual function of the second-order motion perception being more impaired than that of the first-order motion perception. Second-order motion perception requires higher level cortical integration. Hence, higher order visual functions are potentially more affected by normal aging given that they solicit more complex neural networks and that there is an exponential increase in the alternate networks recruited to perform the task during aging.

This study indicates that stimulus type and temporal frequency are determinants in the observed age-related motion integration reduction. Accordingly, stimulus requiring higher level cortical processing would induce greater motion perception deficits in the older population. Moreover, stimulus presented with increasing temporal frequency would elicit greater deficits in motion perception, as evidence of the age-related diminished temporal integration efficiency. These findings can be used when considering the influence of visual functions on mobility. Better understanding of the environmental factors placing older adults at risk of falls can be ensured through knowledge of specific factors impairing motion integration in this particular population.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

REFERENCES

Allard, R., & Faubert, J. (2006). Same calculation efficiency but different internal noise for luminance- and contrast-modulated stimuli detection. *Journal of Vision*, 6(4), 322-334, http://journalofvision.Org/6/4/3/. dokl.O/I 167/6.4.3.

Bertone A, Bettinelli L, Faubert J. (2006) The impact of blurred vision on cognitive assessment. *Journal of Clinical and Experimental Neuropsychology* (accepted).

Bertone A, Faubert J (2006). Demonstrations of decreased sensitivity to complex motion information not enough to propose autism-specific neural etiology. *Journal of Autism and Developmental Disorders*, 36, 55-64.

Bertone A, Mottron, L, Jelinic, P, Faubert J. (2003). Motion perception in Autism: A 'complex' issue. *Journal of Cognitive Neuroscience*, 15, 218-225.

Bertone A, Mottron L, Jelenic P, Faubert J (2005). Enhanced and diminished visuo-spatial information processing in autism depends on stimulus complexity. *Brain*, 128, 2430-2441.

Brosseau-Lachaine, O., Gagnon, I., Forget, R., Faubert, J. (2008) Mild traumatic brain injury induces prolonged visual processing deficits in children. *Brain Injury*, 22(9), 657-668.

Faubert, J. (2002) Visual perception and aging. *Canadian Journal of Experimental Psychology*, 56, 164-176.

Habak, C. & Faubert, J. (2000). Larger effect of aging on the perception of higher-order stimuli. *Vision Research*, 40(8), 943-950.

Karwatsky P, Bertone A, Overbury O, Faubert J (2006). The role of low and higher-level neural mechanisms in glaucoma-related motion perception deficits. *Optometry and Vision Science,* 83, 466-472.

Kogan C S, Bertone A, Cornish K, Boutet I, Der Kaloustian V M, Andermann E, Faubert, J, Chaudhuri A (2004). Integrative cortical dysfunction and pervasive motion perception deficit in fragile X syndrome. *Neurology,* 63, 1634-1639.

Thibault, D. Brosseau-Lachaine, O., Faubert, J., Vital-Durand, F. (2007) Maturation of the sensitivity for luminance and contrast modulated patterns during development of normal and pathological human children. *Vision Research,* 47(12):1561-9

What is claimed is:

1. A device for measuring mild perceptual impairment of a human subject, comprising:
    a generator of stimuli for application to the human subject, each stimuli having at least one parameter, the stimuli including a first-order dynamic stimulus and a second-order dynamic stimulus, the generator being further configured to apply temporal frequency variations to at least one of the first-order and second-order dynamic stimuli;
    a producer, for operation by the human subject, of responses to the stimuli indicative of a perception of the at least one parameter of each stimuli by the human subject, the responses to the stimuli being further indicative of a sensitivity of the human subject to the temporal frequency variations applied to the at least one of the first-order and second-order dynamic stimuli; and
    a processor of the responses of the human subject configured to determine a perceptual signature which is a characteristic pattern of performance determined by the processor measuring luminance sensitivity of the human subject to static and the first order dynamic stimuli and measuring contrast sensitivity of the human subject to static and the second order dynamic stimuli in view of determining if the human subject suffers from mild perceptual impairment;
    wherein the determination by the processor of the perceptual signature is based on the temporal frequency variations applied to the at least one of the first-order and second-order dynamic stimuli.

2. A device for measuring mild perceptual impairment of a human subject as defined in claim 1, wherein the generator of stimuli comprises a screen for displaying an image stimulus, and wherein the processor is connected to the screen for controlling display of image stimuli on the screen.

3. A device for measuring mild perceptual impairment of a human subject as defined in claim 2, wherein the screen comprises two separate screens including a first screen seen by a left eye of the human subject and a second screen seen by a right eye of the human subject.

4. A device for measuring mild perceptual impairment of a human subject as defined in claim 2, wherein the generator of stimuli further comprises binoculars including left and right viewing objectives through which left and right eyes of the human subject, respectively, look at the image stimulus, wherein:
    the left and right viewing objectives each comprise a shutter operated between a closed position and an open position;
    in the open position of the shutter of the left viewing objective, the left eye of the human subject is allowed to see the image stimulus on the screen while, in the closed position of the shutter of the left viewing objective, the left eye of the human subject is prevented from seeing the image stimulus on the screen;
    in the open position of the shutter of the right viewing objective, the right eye of the human subject is allowed to see the image stimulus on the screen while, in the closed position of the shutter of the right viewing objective, the right eye of the human subject is prevented from seeing the image stimulus on the screen; and
    operation of the shutters of the left and right viewing objectives between the open and closed positions enable conduction of tests on the human subject in which the left eye only, the right eye only or both the left and right eyes of the human subject are allowed to see the image stimulus displayed on the screen.

5. A device for measuring mild perceptual impairment of a human subject as defined in claim 1, wherein the generator is further configured to produce a first-order orientation stimulus and a second-order orientation stimulus and the processor is further configured to determine the perceptual signature by measuring a sensitivity of the human subject to the first-order orientation stimulus and to the second-order orientation stimulus.

6. A device for measuring mild perceptual impairment of a human subject as defined in claim 5, wherein the first-order orientation stimulus is a first-order rotation image stimulus.

7. A device for measuring mild perceptual impairment of a human subject as defined in claim 5, wherein the second-order orientation stimulus is a fractal rotation image stimulus.

8. A device for measuring mild perceptual impairment of a human subject as defined in claim 1, wherein the producer of responses to the stimuli comprises an orientation and direction discrimination response box, and wherein the orientation and direction discrimination response box is connected to the processor to supply the responses of the human subject to the stimuli to said processor in which the responses are recorded for further analysis thereof.

9. A device for measuring mild perceptual impairment of a human subject as defined in claim 8, wherein the generator of stimuli comprises a screen for displaying an image stimulus, and wherein the orientation and direction discrimination response box comprises a suitable keyboard to allow the human subject to enter at least one of the following responses:
    whether bars displayed on the screen as image stimulus are vertical or horizontal;
    whether the vertical bars displayed on the screen move toward the left or the right;
    whether the horizontal bars displayed on the screen move upwardly or downwardly;
    whether the bars displayed on the screen are rotating clockwise or counterclockwise;
    regarding shapes displayed on the screen as image stimulus, whether a given target appears in a first or second image presented on the screen.

10. A device for measuring mild perceptual impairment of a human subject as defined in claim 1, wherein the stimuli comprises image stimuli, wherein the processor manipulates the at least one parameter of the image stimulus, wherein the processor determines perceptual sensitivity of the human subject in relation to the at least one manipulated parameter, and wherein, based on responses of the human subject for the at least one parameter of image stimuli, it is established whether the patient suffers from mild perceptual impairment.

11. A device for measuring mild perceptual impairment of a human subject as defined in claim 1, wherein the stimuli are implemented in at least one of the visual, auditory and tactile domains.

12. A device for measuring mild perceptual impairment of a human subject as defined in claim 1, wherein the perceptual signature is usable concurrently with methods of cognitive assessment to build cognitive profiles used for diagnosis of variously neurological conditions.

13. A device for measuring mild perceptual impairment of a human subject as defined in claim 1, wherein the processor performs at least one of the following functions:
- calculate contrast thresholds and sensitivity measures related to responses of the human subject to various stimuli;
- perform statistical analysis by comparing the responses of the human subject to the various stimuli to representative population means to establish normality of abnormality values;
- calculate, produce and supply charts, graphs, or tables showing information data regarding the responses of the human subject to the various stimuli, for evaluation by a physician, neurologist or other medical professional; and
- transmit the information data regarding the responses of the human subject to the various stimuli, to a central server.

* * * * *